United States Patent [19]

Hara et al.

[11] Patent Number: 4,692,690
[45] Date of Patent: Sep. 8, 1987

[54] PATTERN DETECTING APPARATUS

[75] Inventors: Yasuhiko Hara, Machida; Koichi Karasaki, Hadano; Noriaki Ujiie; Akira Sase, both of Katsuta, all of Japan

[73] Assignee: Hitachi, Ltd., Tokyo, Japan

[21] Appl. No.: 686,007

[22] Filed: Dec. 24, 1984

[30] Foreign Application Priority Data

Dec. 26, 1983 [JP] Japan ............... 58-243850
Dec. 26, 1983 [JP] Japan ............... 58-243851

[51] Int. Cl.$^4$ .................................... G01R 31/02
[52] U.S. Cl. ..................... 324/73 PC; 324/158 R; 356/394; 356/398; 358/101; 358/106
[58] Field of Search ......... 324/73 PC, 158 R, 158 D, 324/158 T; 358/101, 105, 106, 111, 113; 356/376, 394, 398; 250/302; 178/105, 106

[56] References Cited

U.S. PATENT DOCUMENTS

| | | | |
|---|---|---|---|
| 4,087,685 | 5/1978 | Froot | 250/302 |
| 4,152,723 | 5/1979 | McMahon et al. | 358/106 |
| 4,305,097 | 12/1981 | Doemens et al. | 358/101 |
| 4,343,553 | 8/1982 | Nakagawa et al. | 358/101 |
| 4,349,277 | 9/1982 | Mundy et al. | 356/376 |
| 4,520,388 | 5/1985 | Kellie | 358/106 |
| 4,536,654 | 8/1985 | Vaerman | 250/302 |

FOREIGN PATENT DOCUMENTS 4898886 1/1973 Japan .

OTHER PUBLICATIONS

"A Digital Video Image Processor for Real-Time X-Ray Subtraction Imaging", by Kruger et al., Optical Engineering, 12/78, vol. 17, #6,358-111, pp. 652-657.

Primary Examiner—Reinhard J. Eisenzopf
Assistant Examiner—W. Burns
Attorney, Agent, or Firm—Antonelli, Terry & Wands

[57] ABSTRACT

A pattern detecting apparatus for inspecting a printed wiring board is disclosed in which a fluorescent image formed by the fluorescent light from the substrate of the printed wiring board and an image formed by the reflected light from the wiring pattern of the printed wiring board are both used because a wiring material which is left on an undesired portion of the substrate and has low reflectivity, is detected only at the fluorescent image and a defective portion of the wiring pattern where a surface layer thereof peels off, is detected only at the image formed by the reflected light, the image used for detecting the above defective portion is preferably formed by the reflected infrared light from the wiring pattern for the reason that infrared light is insensitive to a shallow flaw in the surface of the wiring pattern, and the fluorescent image and the infrared image are processed by a detection circuit, and then compared with each other to detect a pattern defect on the basis of a difference between the images thus processed.

9 Claims, 33 Drawing Figures (MEMORY 54)

LUMINOUS REGION — THICK (MEMORY 56)

THIN (MEMORY 54')

(57)

(59)

(MEMORY 61)

(62)

(MEMORY 54)

LUMINOUS REGION (MEMORY 54')

DARK REGION (159)

9

(MEMORY 161)

FIG. 30
(MEMORY 158)
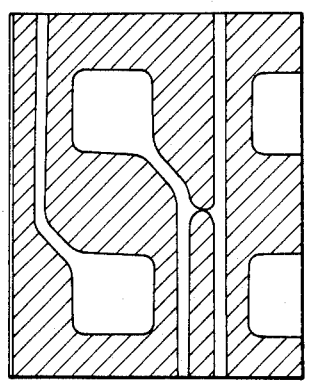
FIG. 31
(MEMORY 164)
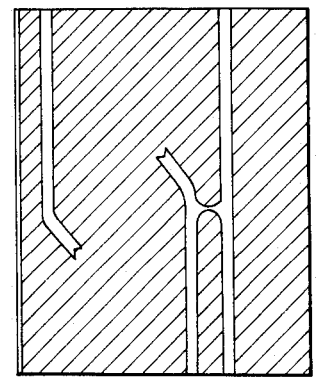
DERIVED FROM
FIG. 26 & FIG. 29
FIG. 32
(MEMORY 165)
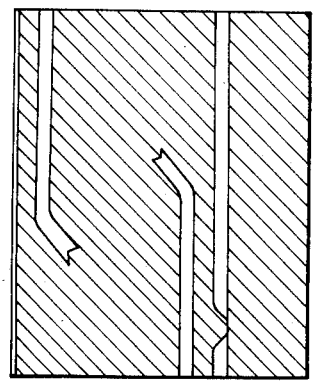
DERIVED FROM
FIG. 27 & FIG. 29
FIG. 33
(166)
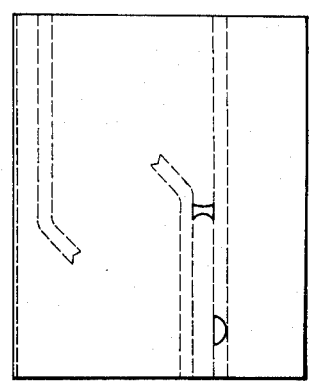

PATTERN DETECTING APPARATUS

The present invention relates to a surface inspecting apparatus using optical means, and more particularly to a pattern detecting apparatus suitable for detecting a short-circuiting portion which is formed on the printed wiring board and has low reflectivity for incident light and a defective portion where a surface layer of the wiring pattern of a printed wiring board has peeled off.

One of conventional pattern detecting apparatuses is disclosed in Japanese Patent Application No. 33909/81. In this conventional pattern detecting apparatus, light having a specified wavelength is selected so that the wiring pattern of a printed wiring board is greatly different in reflectivity for the above light from the insulating substrate of the board, and the wiring pattern. That is, this apparatus utilizes a difference in reflectivity between the wiring pattern and objects to be detected, and the discrimination between the insulating substrate and the wiring pattern is made by means of a light having wavelengths in a limited range in such a condition as not to be easily affected by the surface oxidation of the pattern and the contamination of the surface layer.

However, in the prior art the irregular reflection of a light caused by fine cuts on the pattern surface is judged as a defect by mistake and it is difficult to detect any defect in the form of short-circuit of low light reflection ratio.

Now, the pattern detecting apparatus disclosed in the above-referred to Japanese Patent Application will be explained below in more detail, with reference to FIG. 15. In this apparatus, light reflected from the wiring plane 2' of a printed wiring board 1 is detected by a detector 15, to detect a pattern defect. In FIG. 15, reference numeral 2 designates a wiring pattern, 11 a light source, 12 a lens for converting light emitted from the light source 11 into parallel light rays 31, 13 a semitransparent mirror, and 14 a lens for focussing light 41 which has been reflected back from the wiring plane and has passed through the mirror 13, on the detector 15, to form an image of the wiring plane 2'. In the above apparatus using light which is reflected from a to-be-inspected surface, however, a shallow flaw-in on the wiring pattern such as indicated by reference numeral 5 in FIGS. 13 and 14A may be detected and regarded as defects, though they are not true defects. Further, it is difficult to detect a short-circuiting portion having low resistivity for light such as indicated by reference numeral 6 in FIGS. 13 and 14B.

An object of the present invention is to provide an apparatus for detecting a wiring pattern on a substrate, which can improve the detection capability of prior art, and in which a shallow flaw in the wiring pattern is not regarded as a defect, and not only a short-circuiting portion having low reflectivity for light but also a defective portion where a surface layer of the wiring pattern peels off, can be surely detected.

Another object of the present invention is to provide a method of and an apparatus for detecting a wiring pattern on a substrate, in which a narrow portion of a land caused by the deviation of a through-hole from a predetermined position is not regarded as a defect, and not only a short-cuiting portion having low reflectivity for light but also a defective portion where a surface layer of the wiring pattern peels off, can be surely detected.

In order to attain the above objects, according to the present invention, fluorescent light emitted from the substrate of a printed wiring board or the like is used for detecting a wiring pattern.

Further, in order to detect the wiring pattern more surely, the conventional method using the reflected light from the wiring pattern and the inventive method using the fluorescent light from the substrate are combined with each other. However, the image of that region of the substrate where the wiring pattern is bonded to the substrate, formed by the fluorescent light is different in size from the image of the surface of the wiring pattern formed by the reflected light, since the cross section of the wiring pattern has the form of a trapezoid whose bottom side is placed on the substrate. Accordingly, it is impossible to superpose these images on each other as they are. In the present invention, the pattern image formed by the fluorescent light is contracted, and then combined with the pattern image formed by the reflected light.

Further, in order to carry out both of the detection using the fluorescent light and the detection using the reflected light by a single optical system and to improve the signal-to-noise ratio in a pattern detecting operation, an infrared component contained in light which impinges on the printed wiring board to generate the fluorescent light, is used for forming the reflected light.

In order to attain the latter one of the above objects, according to the present invention, there is provided a method of and an apparatus for erasing the image of a through hole existing in a land from the fluorescent image, by utilizing the fact that the silhouette of the wiring pattern is formed by the fluorescent light. In more detail, the image of the wiring plane formed by the fluorescent light is contracted so that the silhouette of the wiring pattern is extinguished, and then is enlarged so that the image of a land is returned to an original size. Thus, the image obtained after such contraction and enlargement processing contains only the image of the land. Then, the logical product of the above image and the image formed by the fluorescent light is take, to obtain only the image of the wiring pattern.

Now, the optical system and circuit construction of a pattern detecting apparatus according to an aspect of the present invention will first be described, and then characteristic features thereof will be described.

A pattern detecting apparatus according to an aspect of the present invention includes: a first light source for illuminating the wiring plane of a printed wiring board or ceramic wiring board with light; a first detector for detecting the fluorescent light emitted from the substrate of the printed wiring board or ceramic wiring board, a first filter for extracting a light component capable of readily generating the fluorescent light, from the light emitted from the light source; a second filter for cutting off the light reflected from the wiring plane, and for transmitting the fluorescent light from the substrate; a first focussing lens for forming the image of a wiring pattern on the first detector by the fluorescent light; a first semitransparent mirror for directing the light from the first light source, to the wiring plane, and for leading the fluorescent light emitted from the substrate, to the first focussing lens and the first detector; a first electric circuit for subjecting the pattern image formed by the fluorescent light, to analog-to-digital conversion, and for converting the digitized image into a binary pattern image; a first memory for storing the binary pattern image from the first electric circuit; an electric circuit for inverting the polarity of the binary pattern image stored in the first memory, that is, for producing a negative image of the black and white image stored in the first memory, and for contracting the negative image; a second memory for storing the polarity-inverted, contracted pattern image; a second light source for illuminating the wiring plane with light; a second detector for detecting the light reflected from the wiring plane; a second focussing lens for forming an image of the wiring pattern on the second detector by the reflected light; a second semitransparent mirror for directing the light from the second light source, to the wiring plane, and for leading the reflected light to the second focussing lens and the second detector; a second electric circuit for subjecting the pattern image formed by the reflected light, to analog-to-digital conversion, and for converting the digitized image into a binary pattern image; a third memory for storing the binary pattern image from the second electric circuit; an electric circuit for masking the contents of the third memory by the contents of the second memory; and an electric circuit for extracting a defect from the output of the masking circuit, whereby the pattern image formed by the reflected light is masked by the polarity-inverted, contracted one of the pattern image formed by the fluorescent light, to detect the defect. The above pattern detecting apparatus according to an aspect of the present invention can be characterized in the following points.

The first light source, first focussing lens and first semitransparent mirror each concerning the fluorescent light are also used as the second light source, second focussing lens and second semitransparent mirror each concerning the reflected light, respectively.

A superhigh pressure mercury vapor lamp can be used as the light source for illuminating the wiring plane with light.

A dichroic mirror which reflects blue light, transmits red light, and is placed at 45° with an optical axis, is used as the semitransparent mirror for leading the fluorescent light emitted from the substrate and the reflected light from the wiring plane, to the first and second detectors, respectively, through the focussing lens.

The optical system for generating the fluorescent light and for leading it to the focussing lens is also used as the optical system for producing the reflected light and for leading it to the focussing lens.

An infrared component which has escaped through the first filter for extracting a light component capable of readily generating the fluorescent light, is reflected from the wiring plane, and the reflected infrared component is detected by the second detector. An infrared reflecting mirror is provided to separate the fluorescent light from the reflected infrared light and to lead the fluorescent light and reflected infrared light to the first and second detectors, respectively, and thus the extracted component and infrared component of the light emitted from a single light source are used for producing the fluorescent light and reflected light, respectively.

An infrared transmitting mirror may be used for separating the fluorescent light from the reflected infrared light, in place of the infrared reflecting mirror.

The first detector for detecting the fluorescent light is a high-sensitivity detector having spectral sensitivity in a wavelength range from 400 to 700 nm, for example, a saticon ® or a plumbicon ®, each of which is an image pickup tube.

The second detector for detecting the reflected infrared light is a high-sensitivity detector having spectral sensitivity in a wavelength range from 700 to 1,100 nm, for example, a silicon vidicon which is an image pickup tube.

The first filter for extracting the light component capable of readily generating the fluorescent light, is a filter capable of transmitting a small quantity of infrared light, for example, a blue filter B370 or B390.

The second filter for cutting off the reflected one of the light component capable of readily generating the fluorescent light, from the wiring plane, and for transmitting the fluorescent light and reflected infrared light, is a yellow or orange glass plate capable of transmitting light components over a wavelength range from 480 to 560 nm.

A contracted one of the pattern image formed by the fluorescent light is combined with the pattern image formed by the reflected light, to detect a defect.

Although the pattern detecting apparatus according to an aspect of the present invention has been described in the above, according to another aspect of the present invention, there is provided a pattern detecting apparatus which comprises: a light source for illuminating the wiring plane of a printed wiring board or ceramic wiring board with light; a first detector for detecting fluorescent light emitted from a substrate of the printed wiring board or ceramic wiring board; a second detector for detecting infrared light reflected from the wiring plane; a first filter for extracting an exciting light component capable of readily generating the fluorescent light, from the light emitted from the light source; a second filter for cutting the exciting light component reflected from the wiring plane, and for transmitting the fluorescent light from the substrate and the reflected infrared light from the wiring plane; a focussing lens for forming images of a wiring pattern on the first and second detectors; a semitransparent mirror for directing the light from the light source, to the wiring plane, and for leading the fluorescent light from the substrate and the reflected infrared light from the wiring plane, to the first and second detectors, respectively, through the focussing lens; an infrared reflecting mirror for separating the reflecting infrared light from the fluorescent light; a first electric circuit for subjecting the pattern image formed by the fluorescent light, to analog-to-digital conversion, and for converting the digital pattern image thus obtained into a binary pattern image; a first memory for storing the binary pattern image from the first electric circuit; a second electric circuit for subjecting the pattern image formed by the reflected infrared light, to analog-to-digital conversion, and for converting the digital pattern image thus obtained into a binary pattern image; a third memory for storing the binary pattern image from the second electric circuit; a two-stage contraction circuit for contracting the pattern memory stored in the first memory so that the image of the wiring pattern is extinguished; a two-stage enlargement circuit for enlarging the contracted image from the two-stage contraction circuit by a factor corresponding to the two-stage contraction; a fourth memory for storing the image from the two-stage enlargement circuit, that is, the image having been subjected to the two-stage contraction and two-stage enlargement; a one-stage contraction circuit for contracting the pattern image formed by the fluorescent light so that the line width of the pattern image formed by the fluorescent light becomes equal to the line width of the pattern image formed by the reflected infrared light; a second memory for storing a polarity-inverted version of the contracted pattern image from the one-stage contraction circuit; a first masking circuit for making a logical product of the image stored in the third memory and the image stored in the fourth memory; a fifth memory for storing a pattern image outputted from the first masking circuit and based upon the reflected infrared light; a second masking circuit for making a logical product of the image stored in the second memory and the image stored in the fourth memory; a sixth memory for storing a pattern image outputted from the second masking circuit and based upon the fluorescent light; and a defect extracting circuit for performing an exclusive- or operation for the image stored in the fifth memory and the image stored in the sixth memory. Briefly, speaking, in order to obtain both of the advantages of the use of the fluorescent light such as a short-circuiting portion having low reflectivity for light can be detected and the deviation of a through hole from a predetermined position is not regarded as a defect, and the advantage of the use of the reflected infrared light such as a defective portion where a surface layer of wiring pattern peels off, can be detected, an image which is obtained by subjecting the image formed by the fluorescent light, to the two-stage contraction and two-stage enlargement, is used for masking the image formed by the reflected infrared light, and is also used for masking an image which is obtained by subjecting the image formed by the fluorescent light, to the one-stage contraction. By these masking operations, the image of only the wiring pattern is extracted from the image formed by the reflected infrared light, and similarly the image of only the wiring pattern is extracted from the image formed by the fluorescent light. These images of only the wiring pattern are combined by a detect detecting unit, to find a pattern defect.

The present invention will become more apparent from the following detailed descriptions taken in conjunction with the accompanying drawings, in which.

Figure 2:
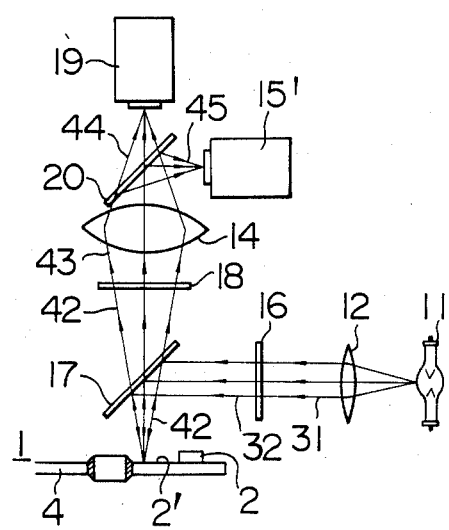
FIG. 2 is a schemaatic diagram showing an embodiment of a pattern detecting apparatus utilizing both fluorescent light and reflected light in accordance with the present invention.
Figure 3:
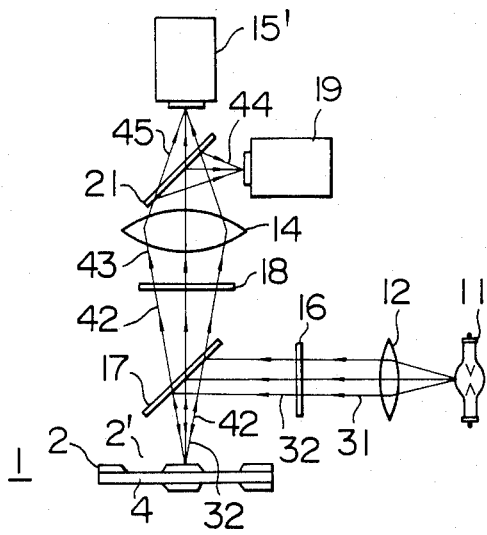
FIG. 3 is a schematic diagram showing a modified version of the embodiment shown in FIG. 2.
Figure 4:
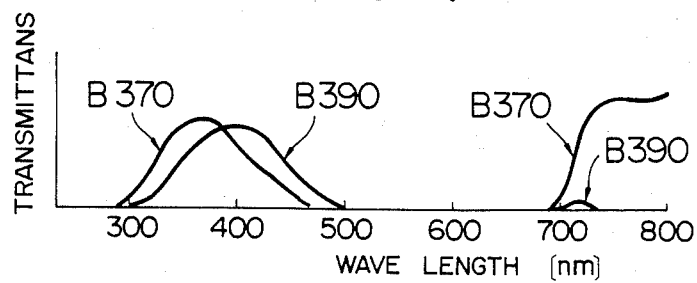
Figure 5:
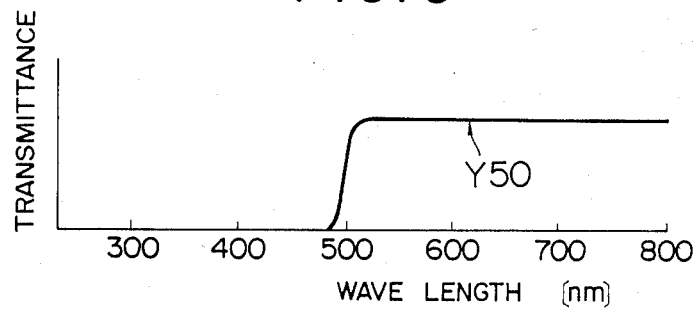
Figure 6:
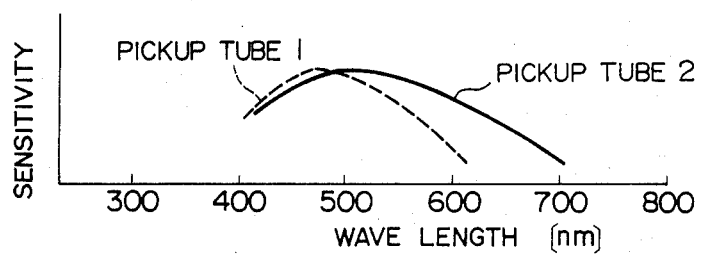
Figure 7:
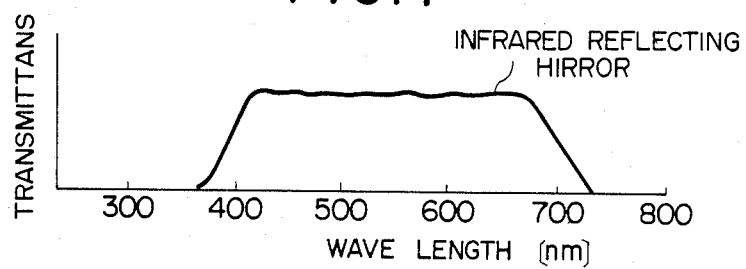
Figure 8:
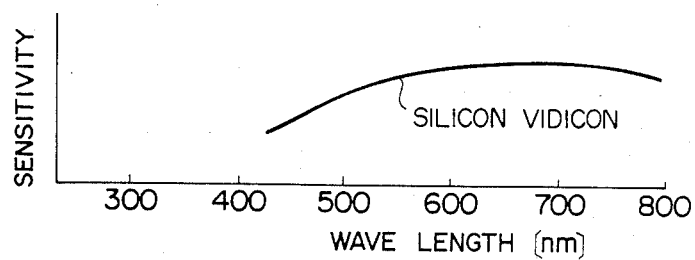
Figure 9:
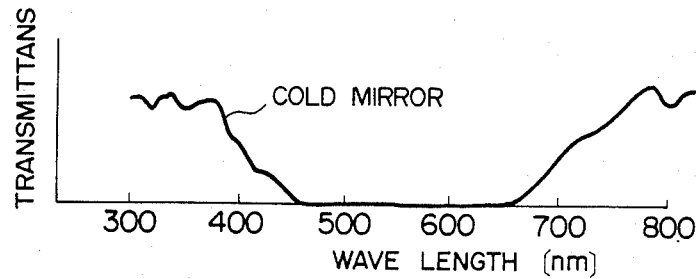
Figure 10:
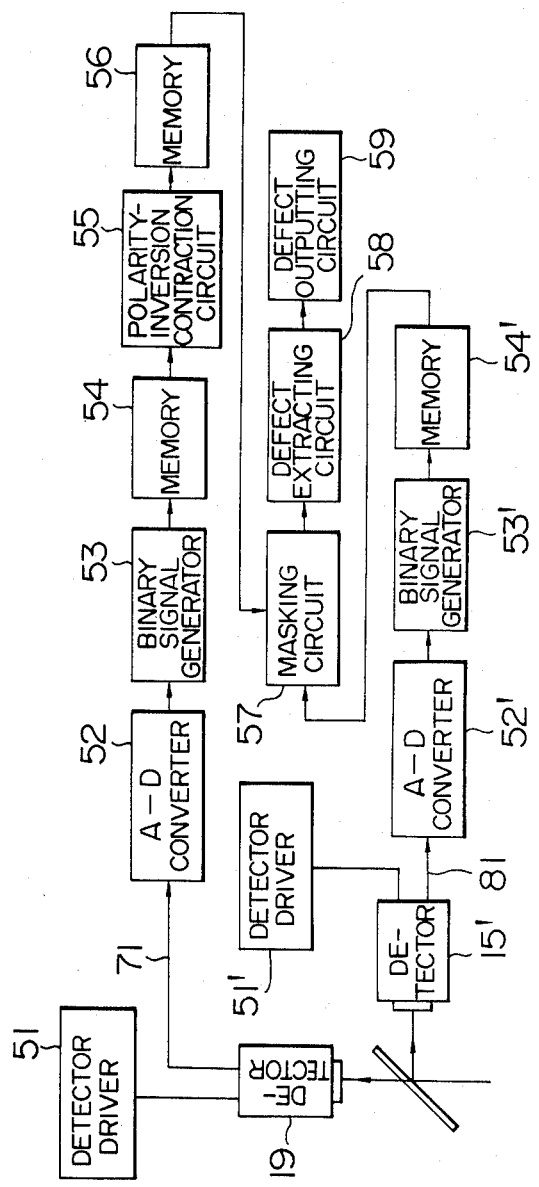
Figure 11:
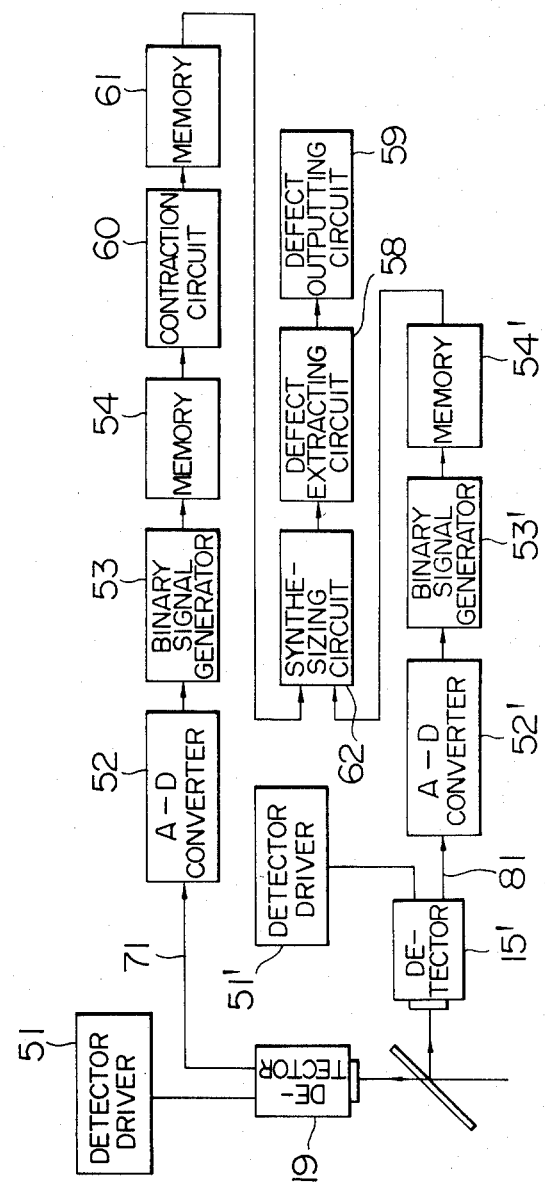
Figure 12:
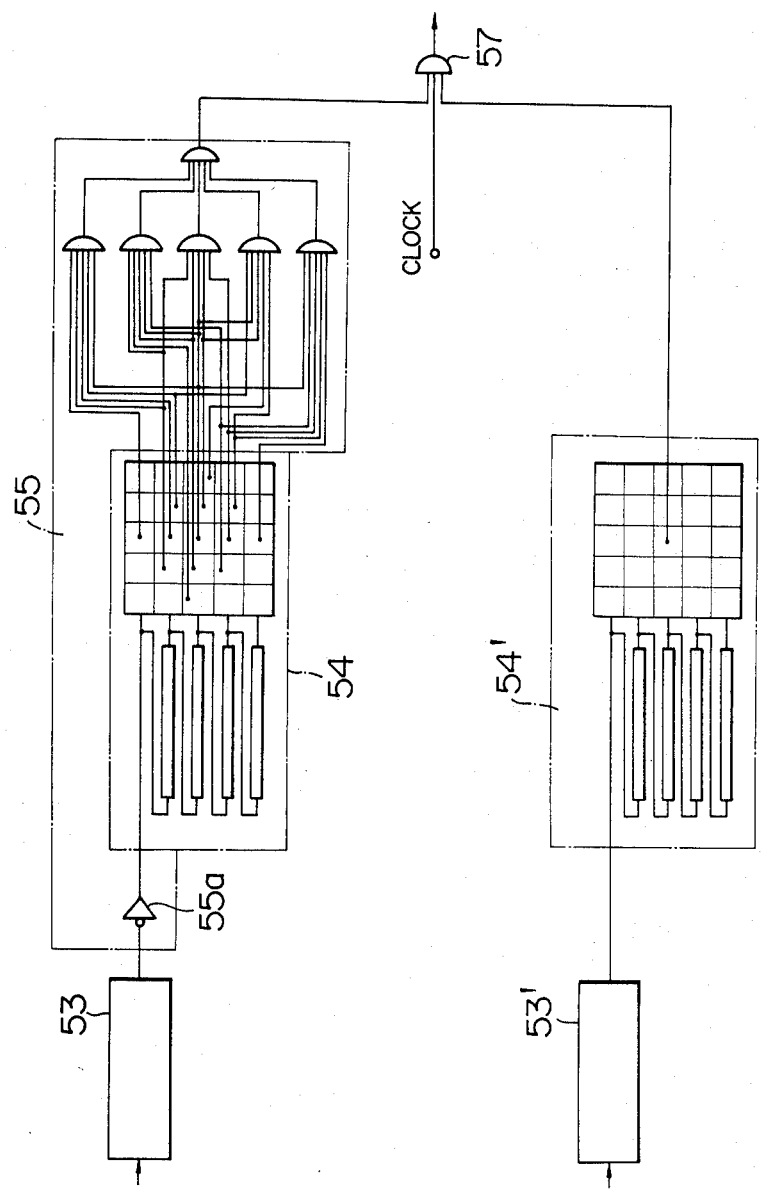
Figure 13:
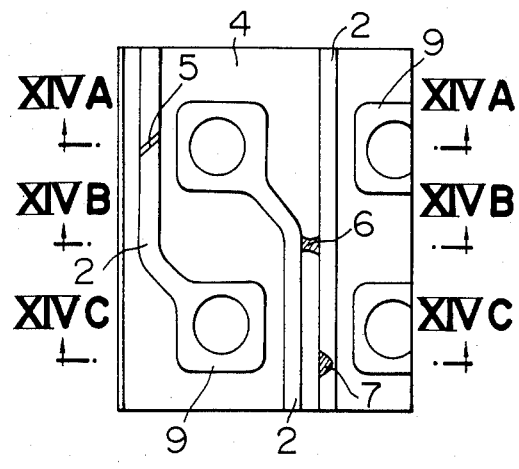
Figure 14A:
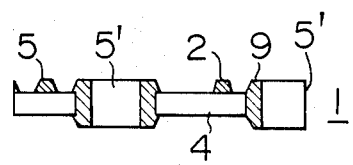
Figure 14B:
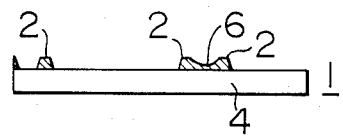
Figure 14C:
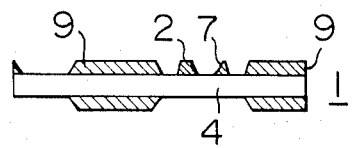
Figure 15:
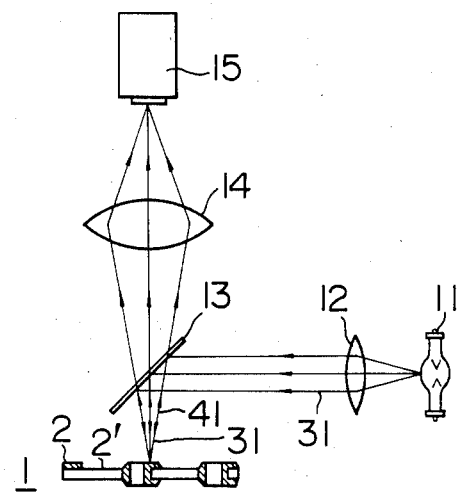
Figure 23:
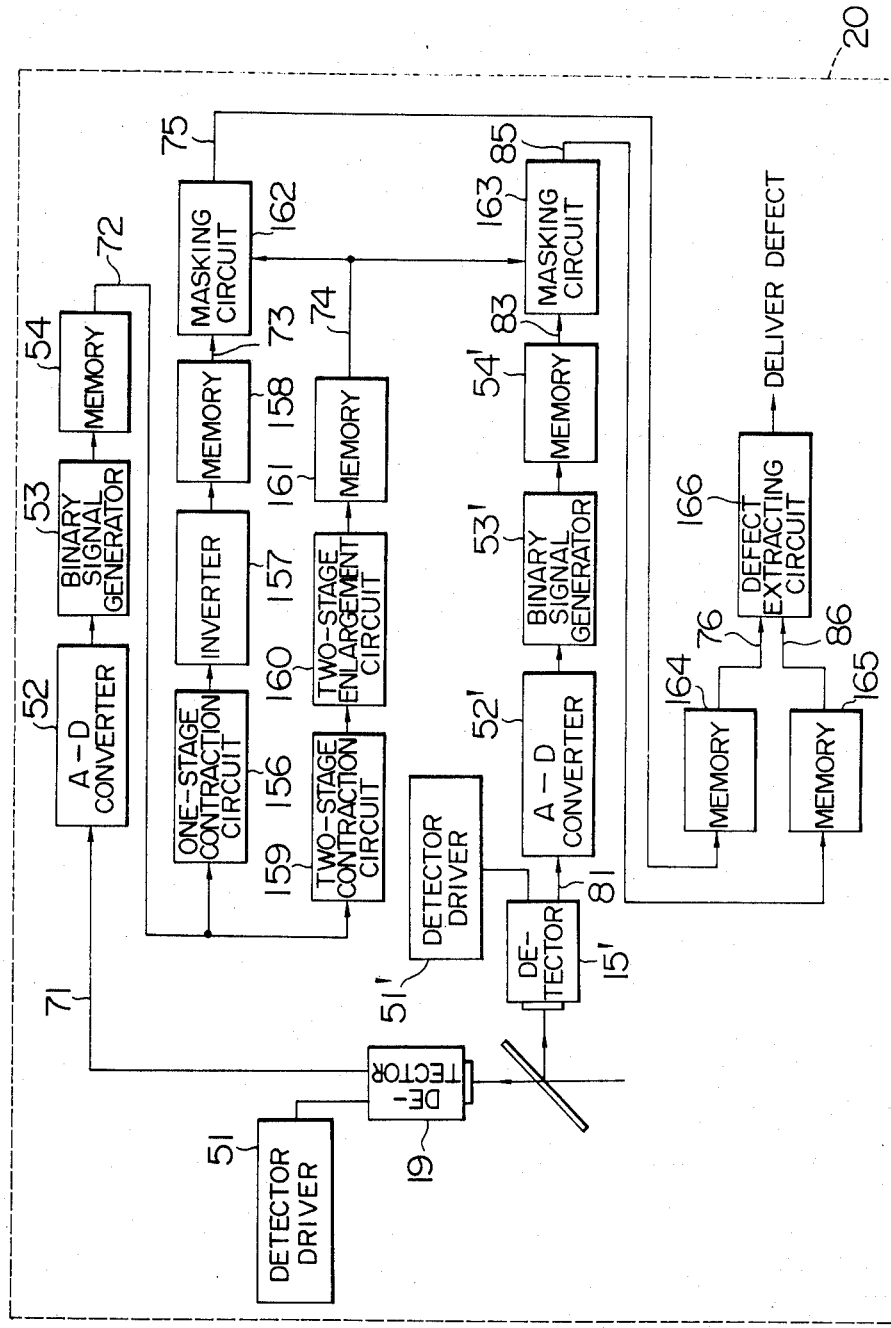
Figure 24:
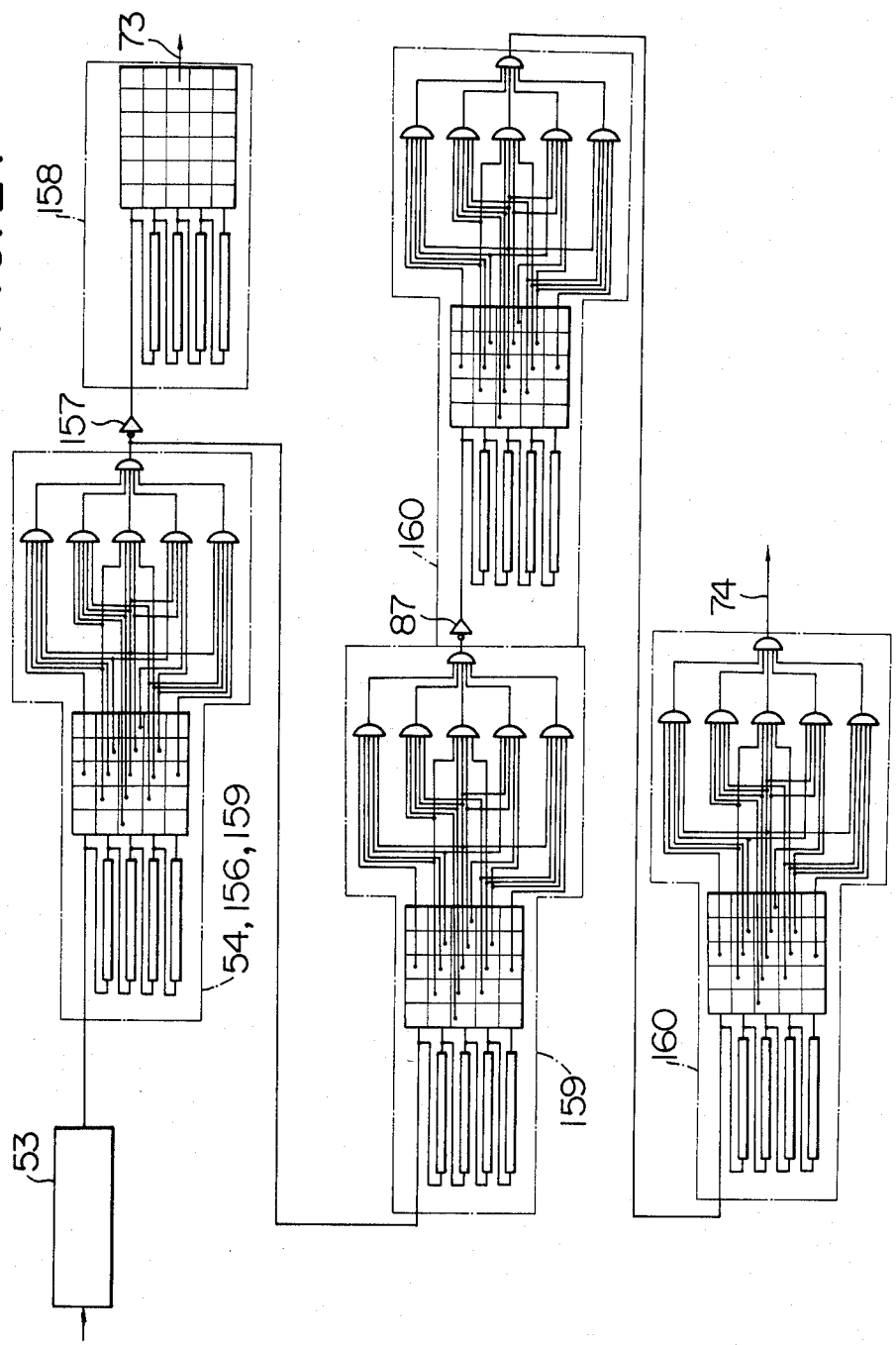
Figure 25:
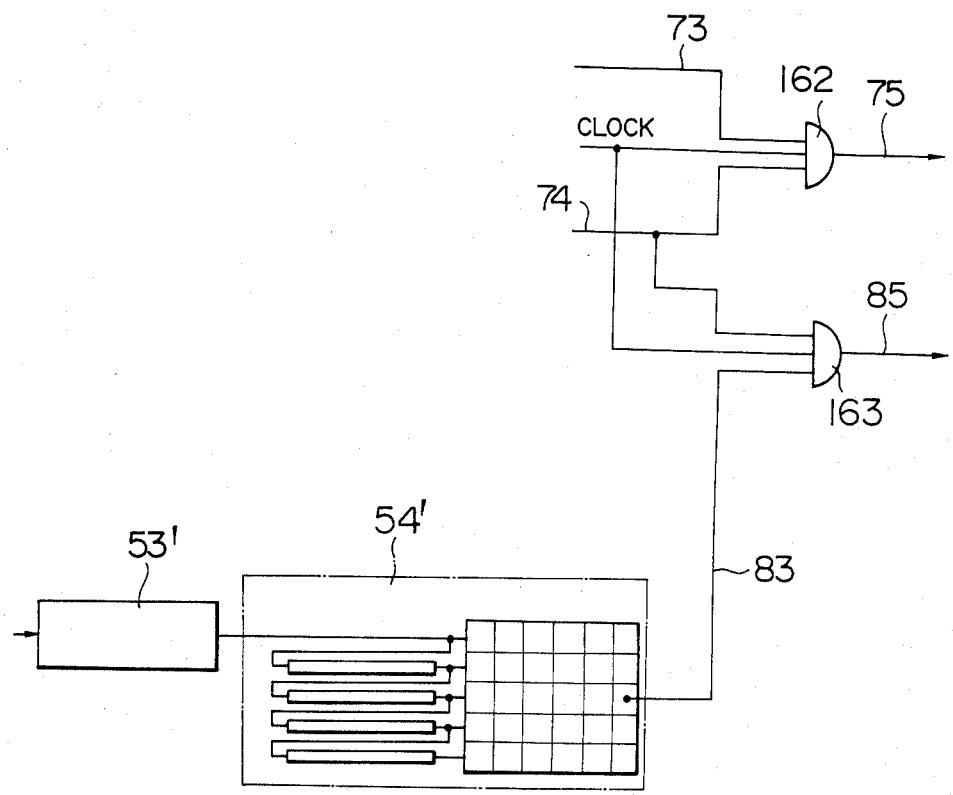

FIGS. 4 and 5 are graphs showing the spectral transmittance characteristics of the filters 16 and 18 shown in both of FIGS. 2 and 3, respectively;

FIG. 6 is a graph showing the spectral sensitivity characteristics of the detector 19 shown in FIGS. 2 and 3;

FIG. 7 is a graph showing the spectral transmittance characteristic of the mirror 20 shown in FIG. 2;

FIG. 8 is a graph showing the spectral sensitivity characteristic of the detector 15' shown in FIGS. 2 and 3;

FIG. 9 is a graph showing the spectral transmittance characteristic of the mirror 21 shown in FIG. 3;

FIG. 10 is a block diagram showing an example of a defect detecting circuit unit included in a pattern detecting apparatus according to the present invention;

FIG. 11 is a block diagram showing another example of the defect detecting circuit unit;

FIG. 12 is a circuit diagram showing details of a circuit part shown in FIG. 10;

FIG. 13 is a plan view showing part of a printed wiring board to be inspected, which board has through holes;

FIGS. 14A, 14B and 14C are sectional views taken along the lines A—A, B—B and C—C of FIG. 13, respectively;

FIG. 15 is a schematic diagram showing a conventional pattern detecting apparatus which utilizes light reflected from a to-be-inspected body;

FIGS. 16 through 22 show images which are obtained when a printed wiring pattern having no through hole is inspected;

FIG. 23 is a block diagram showing a further example of the defect detecting circuit unit;

FIGS. 24 and 25 are circuit diagrams showing details of a circuit part shown in FIG. 23; and FIGS. 26 through 33 show images which are formed in the course of extracting defects from the image of a printed wiring board having through holes.

Now, embodiments of the present invention will be explained below in detail, with reference to FIGS. 1 through 22.

Figure 1:
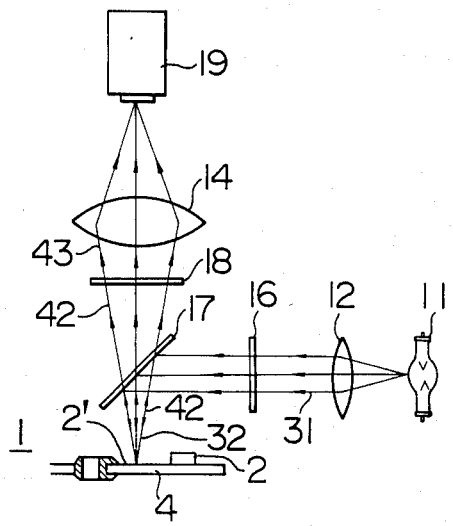
FIG. 1 is a schematic diagram showing an embodiment of a pattern detecting apparatus utilizing fluorescent light in accordance with the present invention.

FIG. 1 shows an embodiment of a pattern detecting apparatus according to the present invention, which embodiment utilizes only fluorescent light. The present embodiment is based upon the following facts. That is, when the wiring plane of a printed wiring board or ceramic wiring board and a resist pattern are illuminated with strong violet or ultraviolet light, fluorescent light is emitted from a substrate and a resist film. The fluorescent light thus generated can be used for forming a negative image of a wiring pattern to be detected. In FIG. 1, reference numeral 1 designates a printed wiring board (or ceramic wiring board) whose substrate can generate fluorescent light when exposed to exciting light, 2 a wiring pattern made of copper, chromium or others, 2' the wiring plane of the board 1, 4 a substrate of the board 1, 11 a high-brightness light source, 12 a condenser lens, 16 a first filter, 17 a semitransparent mirror, 18 a second filter, 14 a focussing lens, and 19 a detector. Light 31 emitted from the light source 11 passes through the condenser lens 12, and reaches the filter 16. The filter 16 extracts light component capable of generating fluorescent light at the substrate 4 of the printed wiring board or ceramic wiring board and the resist film, from the light 31. The filter 16 is formed of, for example, the so-called blue filter B 370. The blue filter 370 has the maximum transmittance at a wavelength of 370 nm, and can transmit light having wavelengths in a range from 300 to 460 nm. The extracted light component is reflected from the semitransparent mirror 17 in such a manner that the direction of outgoing light makes an angle of 90° with the direction of incident light, and is then incident on the board 1. The light incident on the board 1 acts as the exciting light 32 for emitting the fluorescent light from the substrate 4 or resist film. Light 42 containing the fluorescent light from the substrate or resist film and the reflected light from the wiring plane 2' passes through the semitransparent mirror 17, and reaches the filter 18. The filter 18 transmits only the fluorescent light which has wavelengths longer than the wavelengths of the exciting light, to separate the fluorescent light, from the exciting light 32 reflected from the wiring plane 2'. The filter 18 is formed of, for example, the so-called yellow filter Y50, which reflects light having wavelengths less than 500 nm and transmits light having wavelengths greater than 500 nm. The fluorescent light 43 which has been sseparated from the reflected light 32 by the filter 18, is focussed on the photo-electric conversion surface of the detector 19 by the focussing lens 14, and thus a negative image of the wiring pattern 2 is formed. In short, the embodiment shown in FIG. 1 utilizes the fluorescent light emitted from the substrate of the board 1, or the like. Accordingly, a negative image of the wiring pattern can be formed without being affected by a shallow flaw 5 at the surface of the wiring pattern such as shown in FIGS. 13 and 14A, or independently of whether the wiring pattern is glossy or not. Further, when a short-circuiting portion 6 having low reflectivity for light (such as shown in FIGS. 13 and 14B) is left on the substrate of the board 1, the portion 6 prevents the generation of fluorescent light thereat. Accordingly, the short-circuiting portion 6 which is a defect, can be finally detected.

As mentioned above, the wiring pattern can be detected by using the fluorescent light from the substrate, without being affected by a foreign substance on the wiring pattern. However, a defective portion of the wiring pattern where a surface layer of thereof peels off, cannot be found in a negative image of wiring pattern which is formed by the fluorescent light. This defective portion can be detected by using the reflected light from the wiring plane, in addition to the fluorescent light.

Now, explanation will be made of another embodiment of a pattern detecting apparatus according to the present invention, with reference to FIGS. 2 through 15. FIG. 2 shows the above embodiment. In FIG. 2, the same reference numerals as in FIG. 1 designate like parts, and an image becomes a reversed image on a detector 15' by means of an infrared reflecting mirror 20, however, the explanation will be made supposing that there is not such a reversed image. The present embodiment is different from the embodiment of FIG. 1 in that the detector 15' for detecting reflected infrared light and the infrared reflecting mirror 20 are further provided. It is to be noted that the detector 15' is far higher in sensitivity for infrared light than the detector 15 used in the conventional pattern detecting apparatus of FIG. 15. Referring now to FIG. 2, the light 31 emitted from the high-brightness light source 11 (FIG. 2) is incident on the first filter 16 through the condenser lens 12, and the light component capable of readily generating fluorescent light at the substrate 4, that is, the exciting light 32 passes through the first filter 16. The exciting light 32 from the filter 16 is reflected from the semitransparent mirror 17 in such a manner that the direction of outgoing light makes an angle of 90° with the direction of incident light, and is then incident on the wiring plane 2'. The first filter 16 transmits not only the exciting light 32 but also a small quantity of infrared light, and is formed of, for example, the blue filter B370 or B390. A blue-reflecting/red-transmitting dichroic mirror which is placed at 45° with an optical axis, is preferably used as the semitransparent mirror 17. The above dichroic mirror reflects light having short wavelengths, and transmits light having long wavelengths such as the fluorescent light and infrared light. The light 42 containing the fluorescent light from the substrate 4, the intense exciting light 32 reflected from the wiring plane 2' and the infrared light reflected from the wiring plane 2', passes through the semitransparent mirror 17, and is then incident on the second filter 18. The intense exciting light reflected from the wiring plane is cut off by the filter 18. Thus, the light 43 which does not contain the reflected exciting light, passes through the filter 18. The second filter 18 is formed of, for example, the yellow glass filter Y50 capable of effectively separating the fluorescent light from the exciting light. The light 43 having passed through the focussing lens 14 is separated by the infrared reflecting mirror 20 into the fluorescent light 44 and the reflected infrared light 45. The fluorescent light 44 is detected by the detector 19 (namely, the fluorescent detector), and an image of wiring pattern is formed by the fluorescent light 44. While, the reflected infrared light 45 is detected by the detector 15' (namely, the infrared detector), and an image of the wiring pattern is formed by the reflected infrared light. FIGS. 4 through 8 show the characteristics of the optical members. That is, FIG. 4 shows the spectral transmittance characteristic of the first filter 16, FIG. 5 the spectral transmittance characteristic of the second filter 18, FIG. 6 of the spectral sensitivity characteristics of the fluorescent detector 19, FIG. 7 the spectral transmittance characteristic of the infrared reflecting mirror 20, and FIG. 8 the spectral sensitivity characteristic of the infrared detector 15'.

FIG. 3 shows a modified version of the embodiment of FIG. 2. In FIG. 3 an infrared transmitting mirror (that is, a cold mirror) 21 is used in place of the infrared reflecting mirror 20. Further, the arrangement shown in FIG. 3 can be obtained by causing the detectors 19 and 15' shown in FIG. 2 to change positions with each other, and by causing the light paths 44 and 45 to change positions with each other. The operation of the modified version shown in FIG. 3 is the same as that of the embodiment shown in FIG. 2, except that the infrared transmitting mirror 21 is opposite in function for infrared light to the infrared reflecting mirror 20, and therefore further explanation of the modified version will be omitted. FIG. 9 shows the spectral transmittance characteristic of the infrared transmitting mirror 21.

Next, the principle for detecting a defect on the printed wiring board having no through hole will be explained below, with reference to FIGS. 10 through 22.

Figure 16:
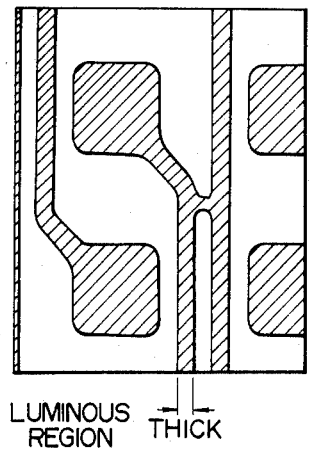
Figure 17:
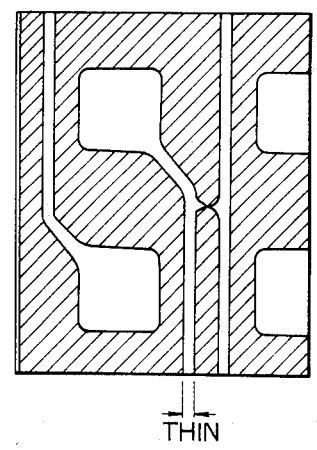
Figure 18:
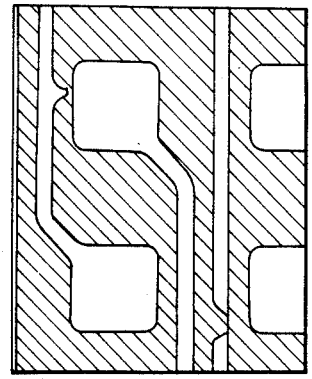
Figure 19:
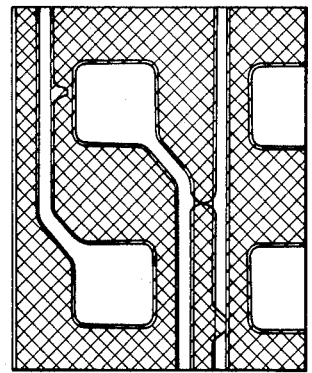
Figure 20:
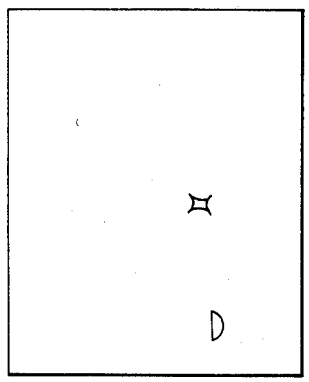

FIG. 10 shows an example of a defect detecting circuit unit used in the present invention. Referring to FIG. 10, a detection signal 71 indicative of the fluorescent pattern image (that is, the pattern image based upon the fluorescent light) detected by the fluorescent detector 19 is converted by an analog-to-digital converter 52 into a digital signal, and then converted by a binary signal generating circuit 53 into a binary signal, which is stored in a first memory 54. The first memory 54 has, for example, a circuit configuration such as disclosed in Japanese Patent Laid-open Specification No. 98886/73, that is, a circuit configuration shown in FIG. 12. FIG. 16 shows a fluorescent pattern image stored in the first memory 54. While, a detection signal 81 indicative of the infrared pattern image (that is, the pattern image based upon the reflected infrared light) detected by the infrared detector 15' is converted by an analog-to-digital converter 52' into a digital signal, and then converted by a binary signal generating circuit 53' into a binary signal, which is stored in a third memory 54' (FIGS. 10 and 18). The third memory 54' has, for example, a circuit configuration disclosed in the above-referred Japanese Patent Laid-Open No. 98886/73 specification, that is, a circuit configuration shown in FIG. 12. FIG. 18 shows an infrared pattern images stored in the memory 54'. The fluorescent pattern images stored in the first memory 54 (namely, the image shown in FIG. 16) is converted by a polarity-inversion/contraction circuit 55 (FIG. 10) into a polarity-inverted, contracted image. That is, a contracted negative image of the black and white image stored in the first memory 54 is formed by the circuit 55. The polarity-inverted, contracted pattern image from the circuit 55 is stored in a second memory 56. FIG. 17 shows the pattern image stored in the second memory 56. As shown in FIG. 12, the second memory 56 may be omitted. In a masking circuit 57, the infrared pattern image stored in the third memory 54' (namely, the image shown in FIG. 18) is masked by the polarity-inverted, contracted fluorescent pattern image stored in the second memory 56 (namely, the image shown in FIG. 17), as shown in FIG. 19. That is, a region corresponding to the remaining region of the polarity-inverted, contracted fluorescent image other than a wiring pattern region, is masked. In a defect extracting circuit 58 (FIG. 10), those areas of the wiring pattern region of the polarity-inverted, contracted fluorescent image which do not exist in the infrared pattern image, are detected. That is, defects can be detected. The defective areas are outputted by a defect outputting circuit 59, as shown in FIG. 20.

In general, the cross section of the wiring pattern of a printed wiring board has a trapezoidal form so that the bottom side kept in contact with the substrate of the printed wiring board is longer than the top side. The fluorescent pattern image shows that portion of the wiring pattern which is kept in contact with the substrate. While, the infrared pattern image shows a top portion of the wiring pattern. Therefore, the infrared pattern image is smaller in line width than the fluorescent pattern image. Accordingly, it is impossible to exactly mask the infrared pattern image by the fluorescent pattern image, and it is required to contract the fluorescent pattern image. An example of the contraction circuit is shown in FIG. 12. In this example, the fluorescent pattern image is contracted by two bits, as will be explained below. Referring to FIG. 12, each of squares included in the first memory 54 corresponds to one bit of the detection signal 71. Five input signals to each of AND gates which are included in the polarity-inversion/contraction circuit 55, are supplied from five squares which make up a cross. The output signa from the AND gate takes a level "1", only when all of the five input signals take the level "1". The contracted pattern image is formed in such a manner that the above output signal is used in lieu of the signal at the center square of the cross, and stored in the second memory. In FIG. 12, reference symbol 55a designates an inverter for inverting the polarity of each bit of the binary signal from the binary signal generating circuit 53 to form a polarity-inverted image. Further, it is to be noted that the circuit configuration of FIG. 12 is shown on the assumption that no time delay occurs in the polarity-inversion/contraction circuit 55.

Figure 21:
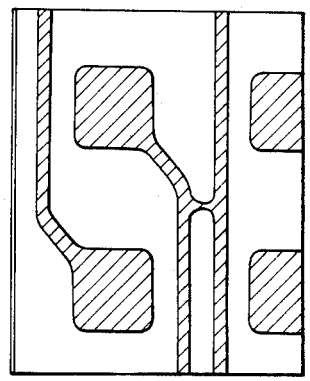
Figure 22:
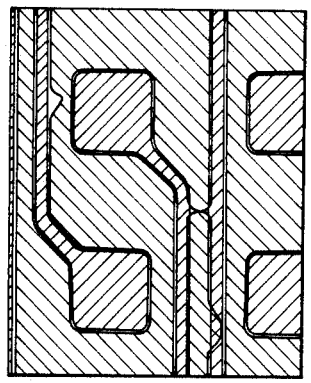

FIG. 11 shows another example of a defect detecting circuit unit used in the present invention. In FIG. 11, the same reference numerals as in FIG. 10 designate like parts. The circuit unit shown in FIG. 11 is different from that shown in FIG. 10 in that a contraction circuit 60 is used in place of the polarity-inversion/contraction circuit 55. That is, the binary pattern image from the binary signal generating circuit 53 is contracted without being inverted in polarity, and then stored in a second memory 61 (FIG. 11). FIG. 21 shows the pattern image stored in the second memory 61. The contracted pattern image stored in the memory 61 (namely, the image shown in FIG. 21) and the infrared pattern image stored in the third memory 54' (namely, the image shown in FIG. 18) are combined by a synthesizing circuit 62. FIG. 22 schematically shows the pattern images thus combined. In the defect extracting circuit 58 (FIG. 11), areas where the wiring pattern region of the contracted pattern image and the remaining region of the infrared pattern image other than the wiring pattern region overlap each other, are extracted and regarded as defects. The defects thus extracted are outputted by means of the defect outputting circuit 59. In other words, those areas in FIG. 22 where a first group of oblique lines overlaps with a second group of oblique lines perpendicular to the first group of oblique lines, are delivered as defects. The defective areas thus delivered are the same as those shown in FIG. 20.

Next, explanation will be made of the defect detection in the case where a printed wiring board has through holes, with reference to FIGS. 23 through 33.

Figure 26:
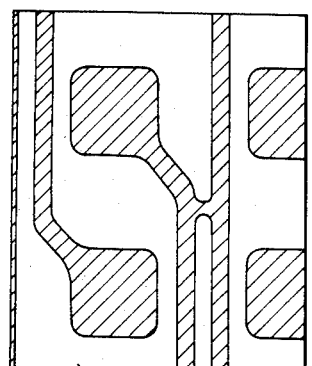

FIG. 23 shows a further example of a defect detecting circuit unit used in the present invention corresponding to FIGS. 10 and 11. In FIG. 23, the same reference numerals as in FIGS. 10 and 11 designate like parts. Referring to FIG. 23, the detection signal 71 indicative of the fluorescent image detected by the fluorescent detector 19 is converted by the analog-to-digital converter 52 into a digital signal, and then converted by the binary signal generating circuit 53 into a binary signal, which is stored in the first memory 54. The first memory has, for example, a circuit configuration described in the previously-referred Japanese Patent Laid-Open Specification No. 98886/73, that is, a circuit configuration shown in FIG. 24. FIG. 26 shows an example of the fluorescent image stored in the first memory 54 (FIG. 23), and the image of FIG. 26 corresponds to the printed wiring board shown in FIG. 13. While, the detection signal 81 indicative of the infrared image detected by the infrared detector 15' (FIG. 23) is converted by the analog-to-digital converter 52' into a digital signal, and then converted by the binary signal generating circuit 53' into a binary signal, which is stored in the third memory 54'.

Figure 27:
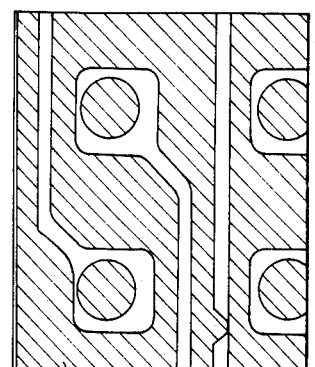
Figure 28:
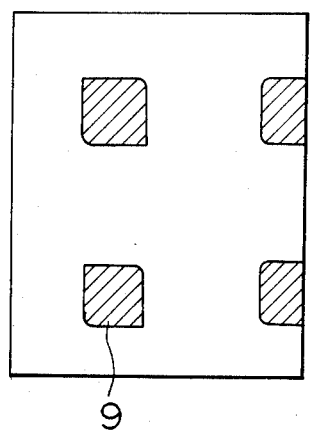
Figure 29:
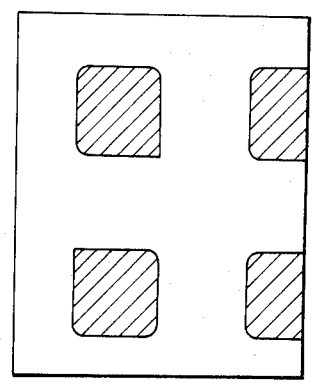

FIG. 27 shows an example of the infrared image stored in the third memory 54', and the image of FIG. 27 corresponds to the printed wiring board shown in FIG. 13. The fluorescent image stored in the first memory 54 (FIG. 23) is sent to both a two-stage contraction circuit 159 and a one-stage contraction circuit 156, in the form of an electric signal 72. The two-stage contraction circuit 159 has the same circuit configuration as described in the above-referred Japanese Patent Laid-open Specification No. 98886/73, and contracts the fluorescent image so that the image of the wiring pattern 2 (FIG. 13) is extinguished. FIG. 28 shows a fluorescent image obtained after the two-stage contraction processing 159 (FIG. 23). The signal 72 thus processed is sent to a two-stage enlargement circuit 160 (FIG. 23). The two-stage enlargement circuit 160 has the same circuit configuration as described in the above-mentioned Japanese Patent Laid-open Specification No. 98886/73, and enlarges the image of a land 9 (shown in FIG. 28) to an original size. The fluorescent image thus enlarged is stored in a fourth memory 161. FIG. 29 shows the fluorescent image stored in the fourth memory 161, that is, the image having been subjected to the two-stage contraction and two-stage enlargement. The one-stage contraction circuit 156 (FIG. 23) has the same circuit configuration as described in the Japanese Patent Laid-open Specification No. 98886/73, and contracts the fluorescent image so that the line width of wiring pattern 2 at the fluorescent image is equal to the line width of wiring pattern 2 at the infrared image. A binary signal indicative of the contracted fluorescent image is sent from the one-stage contraction circuit 156 to an inverter 157, to be inverted in polarity. The polarity-inverted, contracted fluorescent image from the inverter 157 is stored in a second memory 158. FIG. 30 shows the fluorescent image stored in the second memory 158, that is, the fluorescent image which has been subjected to the one-stage contraction and inverted in polarity. An electric signal 73 read out of the second memory 158 and an electric signal 74 read out of the fourth memory 161 are sent to a masking circuit 162, to take the logical proeuct of the signals 73 and 74, thereby forming a fluorescent image in which the image of the land 9 is extinguished and only the image of the wiring pattern 2 is left. An electric signal 75 indicative of the fluorescent image thus formed is sent to a sixth memory 164, and thus the above image is stored in the memory 164. FIG. 31 shows the fluorescent pattern image stored in the sixth memory 164. An electric signal 83 read out of the third memory 54' and the electric signal 74 read out of the fourth memory 161 are sent to another masking circuit 163, to take the logical product of the signals 83 and 74, thereby forming an infrared image in which the image of the land 9 is extinguished and only the image of the wiring pattern 2 is left. An electric signal 85 indicative of the infrared image thus formed is sent to a fifth memory 165, and thus the above infrared image is stored in the memory 165. FIG. 32 shows the infrared pattern image stored in the fifth memory 165. A short-circuiting portion having low reflectivity for light (that is, the portion 6 shown in FIGS. 13 and 14B) is detected at the fluorescent image of FIG. 31, and a defective portion where a surface layer of the wiring pattern 2 peels off (that is, the portion 7 shown in FIGS. 13 and 14C) is detected at the infrared image of FIG. 32. An electric signal 76 read out of the sixth memory 164 and an electric signal 86 read out of the fifth memory 165 are sent to a defect detecting circuit 166, to perform an exclusive- or operation for the signals 76 and 86, thereby extracting defects (solid lines). FIG. 33 shows the images of defects extracted by the defect extracting circuit 166.

FIGS. 24 and 25 are circuit diagrams showing the circuit construction of FIG. 23 in more detail. Since the fourth memory 161 is not always required, the memory 161 is omitted in FIG. 24. Incidentally, an inverter 87 (FIG. 24) is provided on the input side of a two-stage contraction circuit, and the combination of the inverter 87 and the two-stage contraction circuit acts as the two-stage enlargement circuit 160.

As has been explained in the foregoing, according to the present invention, a fluorescent image formed by the fluorescent light from the substrate of a printed wiring board or ceramic wiring board is combined with an infrared image formed by the reflected infrared light from the wiring plane of the above board, to detect a defect. Thus, a shallow flaw in and a foreign substance on a wiring pattern are never regarded as defects, but a short-circuiting portion having low reflectivity for light and a defective portion where a surface layer of wiring pattern peels off, are surely detected. Further, the image of a land can be removed from the fluorescent and infrared images of the wiring plane, and therefore there is no fear of the deviation of a through hole from a predetermined position, being regarded as a defect.

We claim:

1. A pattern detecting apparatus for inspecting a body which has a wiring pattern on a material capable of generating fluorescent light, comprising:
    a light source which emits light having both an exciting light component for generating said fluorescent light from a surface of said material and an infrared light component which is separable from the exciting light component for producing reflected light from a surface of the said wiring pattern;
    a first filter which transmits not only said exciting light component but also said infrared light component from the said light source;
    a first mirror which directs light received from said first filter to the said body and which transmits fluorescent light from the body and reflected light from the body;
    a second filter which transmits the fluorescent light received via said first mirror and the reflected light received via said first mirror, and which removes all exciting light reflected from the body through the first mirror;
    an optical system which includes a second mirror, a fluorescent light detector, a reflected-light detector and a lens for focussing the fluorescent light received from said second filter on said fluorescent-light detector via said second mirror and for focussing the reflected light received from said second filter on said reflected-light detector via said second mirror; and
    a detection circuit including means for contracting, enlarging and masking pattern images detected by the said detectors.

2. A pattern detecting apparatus according to claim 1, wherein said second mirror included in the said optical system transmits light components in the range of wavelengths between 400 nm and 700 nm.

3. A pattern detecting apparatus according to claim 1, wherein said second mirror included in the said optical system reflects light components in the range of wavelengths between 450 nm and 650 nm.

4. A pattern detecting apparatus according to claim 1, wherein said detection circuit further comprises:
    a first series circuit including an A/D converter, a binary signal generator and a first memory, the A/D converter being connected to receive an analog signal from said fluorescent-light detector;
    a second series circuit including an A/D converter, a binary signal generator and a second memory, the A/D converter being connected to receive an analog signal from said reflected-light detector;
    inverting and contracting means connected to said first series circuit for inverting in polarity and contracting data stored in said first memory;
    masking circuit means connected to receive outputs of said second series circuit and said inverting and contracting means for masking one output with another output; and
    an extracting circuit which extracts and outputs defect signals on the basis of an output of said masking circuit means.

5. A pattern detecting apparatus according to claim 1, wherein said detection circuit further comprises:

a first series circuit including an A/D converter, a binary signal generator and a first memory, the A/D converter being connected to receive an analog signal from said fluorescent-light detector;

a second series circuit including an A/D converter, a binary signal generator and a second memory, the A/D converter being connected to receive an analog signal from said reflected-light detector;

contracting means connected to said first series circuit for contracting data stored in said first memory;

synthesizing circuit means connected to receive outputs of said second series circuit and said contracting means for synthesizing said outputs to correlate data represented thereby; and an extracting circuit which extracts and outputs defect signals on the basis of an output of said synthesizing circuit means.

6. A pattern detecting apparatus according to claim 1, wherein said wiring pattern includes lands, and said detection circuit comprises:

a first series circuit including an A/D converter, a binary signal generator and a first memory, the A/D converter being connected to receive an analog signal from said fluorescent-light detector;

a second series circuit including an A/D converter, a binary signal generator and a second memory, the A/D converter being connected to receive an analog signal from said reflected-light detector;

land-isolating circuit means connected to receive an output of said first series circuit for contracting that output to the extend of extinguishing wiring patterns among lands;

contracting and inverting means connected to said first series circuit for inverting in polarity and contracting data stored in said first memory;

a first masking circuit connected to receive an output of said land-isolating circuit means and an output of said contracting and inverting means for masking one output with the other output;

a second masking circuit connected to receive an output of said land-isolating circuit means and an output of said second series circuit for masking one output with the other output; and an extracting circuit which extracts and outputs defect signals from outputs of said first and second masking circuits.

7. A pattern detecting apparatus according to claim 1, wherein the said fluorescent-light detector is an image pickup device that is sensitive to light components in the range of wavelengths between 400 nm and 600 nm.

8. A pattern detection apparatus according to claim 1, wherein said reflected-light detector is an image pickup device that is sensitive to light components in the range of wavelengths between 400 nm and 1000 nm.

9. A pattern detecting apparatus according to claim 1, wherein the said fluorescent-light detector is an image pickup device that is senstive to light components in the range of wavelengths between 400 nm and 700 nm.

* * * * *